United States Patent [19]

Nelson et al.

[11] Patent Number: 5,482,207
[45] Date of Patent: Jan. 9, 1996

[54] SYSTEM FOR FACILITATING THE REMOVAL AND SAFE DISPOSITION OF MEDICAL NEEDLES

[75] Inventors: Mark Nelson, Sandy; David Vangeison, Salt Lake City; Phillip K. Evans, Murry; Robert Wells, Salt Lake City, all of Utah

[73] Assignee: Life Medical Technologies, Inc., Salt Lake City, Utah

[21] Appl. No.: 235,388

[22] Filed: Apr. 29, 1994

[51] Int. Cl.$^6$ ................................................. B65D 91/00
[52] U.S. Cl. ........................................ 232/43.2; 206/366
[58] Field of Search ................................. 206/366, 365; 232/43.2, 43.1; 220/905, 906; 604/110

[56] References Cited

U.S. PATENT DOCUMENTS

| | | | |
|---|---|---|---|
| 4,786,280 | 11/1988 | Maeda | 604/110 |
| 4,798,587 | 1/1989 | Willoughby | 604/110 |
| 4,862,573 | 9/1989 | Kelson et al. | 206/366 |
| 4,986,811 | 1/1991 | Thead et al. | |
| 4,989,307 | 2/1991 | Sharpe et al. | |
| 4,995,871 | 2/1991 | Sasaki et al. | 604/110 |
| 5,188,598 | 2/1993 | Thead et al. | |
| 5,277,868 | 1/1994 | Langford | 206/366 |
| 5,356,383 | 10/1994 | Daly et al. | 206/366 |
| 5,356,385 | 10/1994 | Latini | 604/110 |

*Primary Examiner*—Michael J. Milano
*Attorney, Agent, or Firm*—M. Reid Russell

[57] ABSTRACT

A closed automatic system for removing (for facilitating the removal) and safely storing potentially contaminated medical (or other) needles in which the operator only uses one hand to operate the system. The user simply inserts a syringe with needle attached in the opening provided in the top of the device and resists the rotation of the needle hub after the hub is engaged by the motor driven cams. Sensors detect the presence of the needle and cause the motor to start driving a chuck mechanism (through a shaft to which gears are attached) which engages the needle and rotates it a predetermined, but changeable, number of times sufficient to disengage the needle from the syringe. The operator then removes the syringe and the needle drops or has dropped into the safe. The system has a counter which counts the number of actuations of the needle sensor. When a predetermined limit is reached the device signals the operator that the safe is nearly full. A further fixed number of needles can then be removed, when that limit is reached, a fuse on the safe is blown causing the system to be inoperative until a new box is installed. Removal of the box also causes the fuse to be blown and the circuit is disabled until a new box is inserted. The safe storage box contains a tab which when fixed in the locked position can not be opened except upon the application of substantial force with a tool. The system uses a Motorola 705 EPROM or similar microcontroller.

9 Claims, 8 Drawing Sheets

FIG. 4

SYSTEM FOR FACILITATING THE REMOVAL AND SAFE DISPOSITION OF MEDICAL NEEDLES

BACKGROUND OF THE INVENTION

The present invention relates to the safe disposal of needles which may be contaminated by blood or other fluids. The needles for disposal are attached to syringes using rotatable connectors, typically, but not limited to, threaded luer lock or luer slip types. In particular the present invention relates to a system and structure for facilitating the removal of potentially contaminated needles and depositing them into a container in an operation which requires the operator to use only one hand and virtually no physical effort. The system and structure employ at least one electrically powered and controlled rotating device for removing the needles. The system uses feedback control subsystems for operating and controlling the rotating device, for limiting the number of needles which can be placed in a single storage container and for positioning the needle receiver in a predetermined configuration.

The basic problem to be solved in the field is the safe disposal of used (possibly bloodborne pathogen contaminated) needles with as close to zero risk of needle contact with personnel who use the needles as is possible. Greater risk to personnel is present when the needle removal device requires two hands or one hand with significant physical force or significant manual dexterity such as when reinserting the needle into its protective sheath. Greater risk to personnel is also present when the needles are not placed in a tamper proof container or when the container can overfill. A device which signals its full condition is safer to users than one which is merely in a jammed (inoperative) condition without otherwise signalling its jammed or full status.

FIELD OF THE INVENTION

The present invention relates to the field of the automated safe handling of needles (often called "sharps" in the trade) attached to syringes. The present invention particularly relates to a feedback controlled system in which the operator need use only one hand and minimal physical effort and in which the needles are, when removed, deposited in a tamper proof box which cannot be overloaded and which will not permit further needle removal until the full container is removed.

DESCRIPTION OF THE PRIOR ART

The closest prior art known to the applicants are U.S. Pat. No. 4,989,307 to Sharpe et al., U.S. Pat. Nos. 4,986,811 and 5,188,598, both to Thead et al. These patents disclose needle removal devices with storage of the removed needles in a separate container. The Sharpe patent discloses the general idea of using a photosensor to start the motor. No feedback loop is either shown or described in the Sharpe et al patent. The patents to Thead et al show a needle removal device in which the operator provides the power to engage and rotate the needle removal device. The Thead '598 patent discloses a needle remover which has a mechanical locking device for limiting the number of needles placed in the storage or disposal container. The locking structure made of a number of gears with rotation limiting cutouts is contained in the disposable container.

SUMMARY OF THE INVENTION

The present invention teaches a closed system for removing and safely storing potentially contaminated medical (or other) needles in which the operator only uses one hand to operate. The system is essentially wholly automatic after the needle or other "sharp" is inserted.

The user inserts a syringe with needle attached in the opening provided in the top of the device and resists the rotation of the needle hub after the hub is engaged by the motor driven cams. Sensors detect the presence of the needle and cause the motor to rotate a chuck type mechanism (through a shaft to which gears are attached) which engages the needle and rotates it a predetermined number of times sufficient to disengage the needle from the syringe. The operator then removes the syringe and the needle drops or has dropped into the safe, as the motor reverses and the chuck opens.

The device has a counter which counts the number of actuations. When a predetermined limit is reached the device signals the operator that the safe is nearly full. A further fixed number of needles can then be removed. When that limit is reached, a fuse (acting functionally as a switch) on the safe is blown causing a signal to be sent to the microcontroller to signal the full condition of the safe and rendering the device inoperative. A new safe, with an integral fuse, is installed completing the circuit and thereby making the device operative. Removal of the safe also causes the fuse to be blown and the circuitry is disabled until a new safe with fuse is inserted. The safe contains a tab which when fixed in the locked position can not be opened except upon the application of substantial force with a tool.

DESCRIPTION OF THE PREFERRED EMBODIMENT

Figure 1:
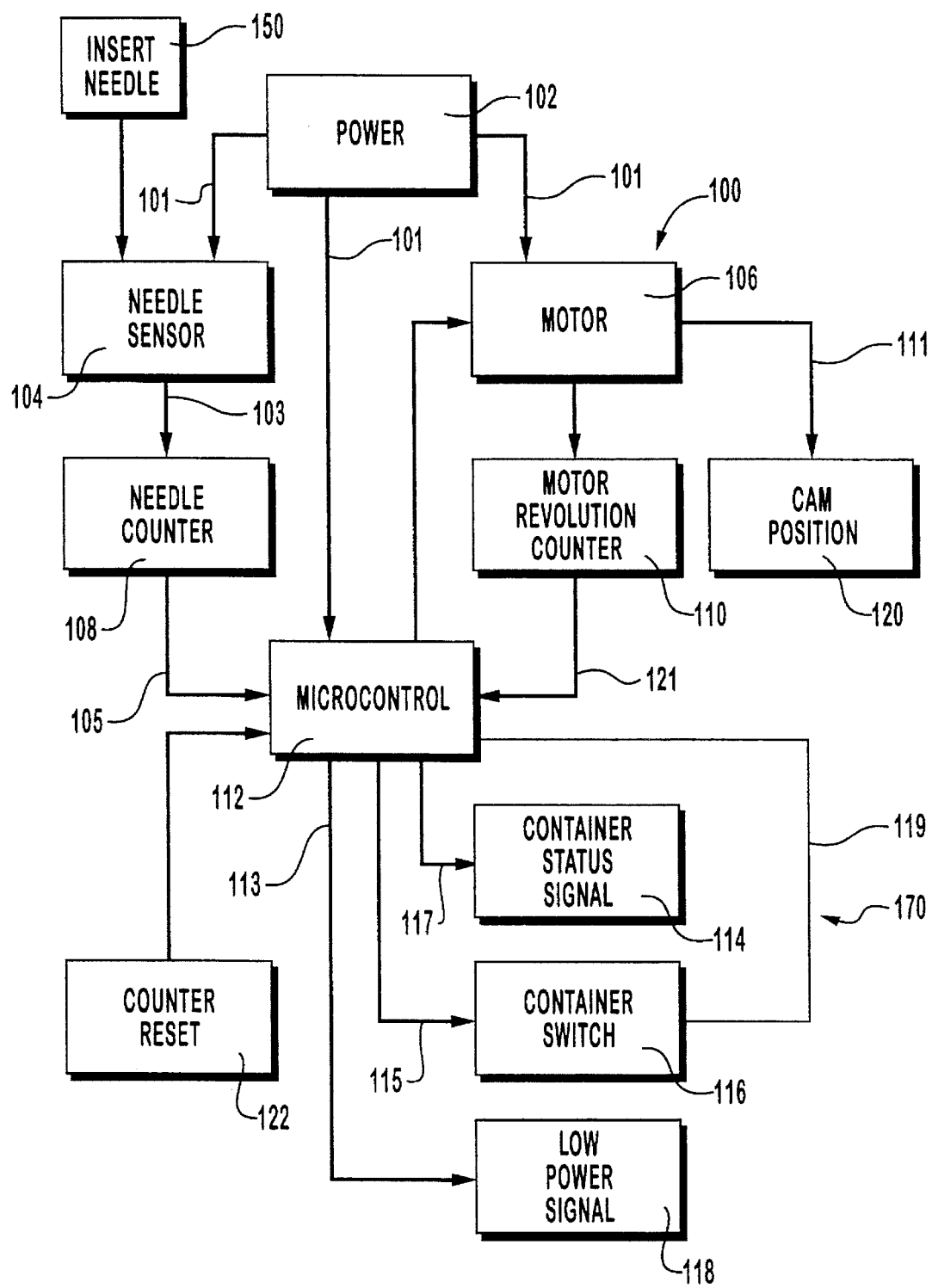
FIG. 1 shows a block diagram of the system of one embodiment of the present invention.

FIG. 1 is a perspective view of the first embodiment of the present invention showing the present invention generally by the number 100. A source of power 102 which can be from either an electrical outlet or from batteries is fed by wires 101 to a needle sensor 104, an electric motor 106 and an integrated circuit (microcontroller) 112.

The needle sensor 104 is formed from a pair of light emitting and sensing diodes (or from an infra-red light emitting diode and photo transistor pair) which sense the presence of the needle by the interruption of the beam of light which may be pulsed infra-red light. The output of the needle sensor is fed by wire 103 to a first counter 108 which then counts the number of needles and provides a signal to a microcontroller 112 (Motorola 705 microprocessor which has a pre-determined program etched or burned in it). The output of the microcontroller is fed by wires 107, 113, 115, 117 to motor 106, low power sensor 118, container switch (fuse) 116 and container status signal 114.

The output of motor 106 is fed by wire 109 to second counter 110 whose output is fed by wire 121 back to microcontroller 112 to form a first feedback loop 160. A second feedback loop 170 is formed by wire 119 feeding the output of switch 116 back to microcontroller 112. The output of motor 106 is also be fed by line 111 to drive gear 120 to control the actuation of the drive gears and cams and the final position of the gears and cams at the end of each cycle.

Figure 2:
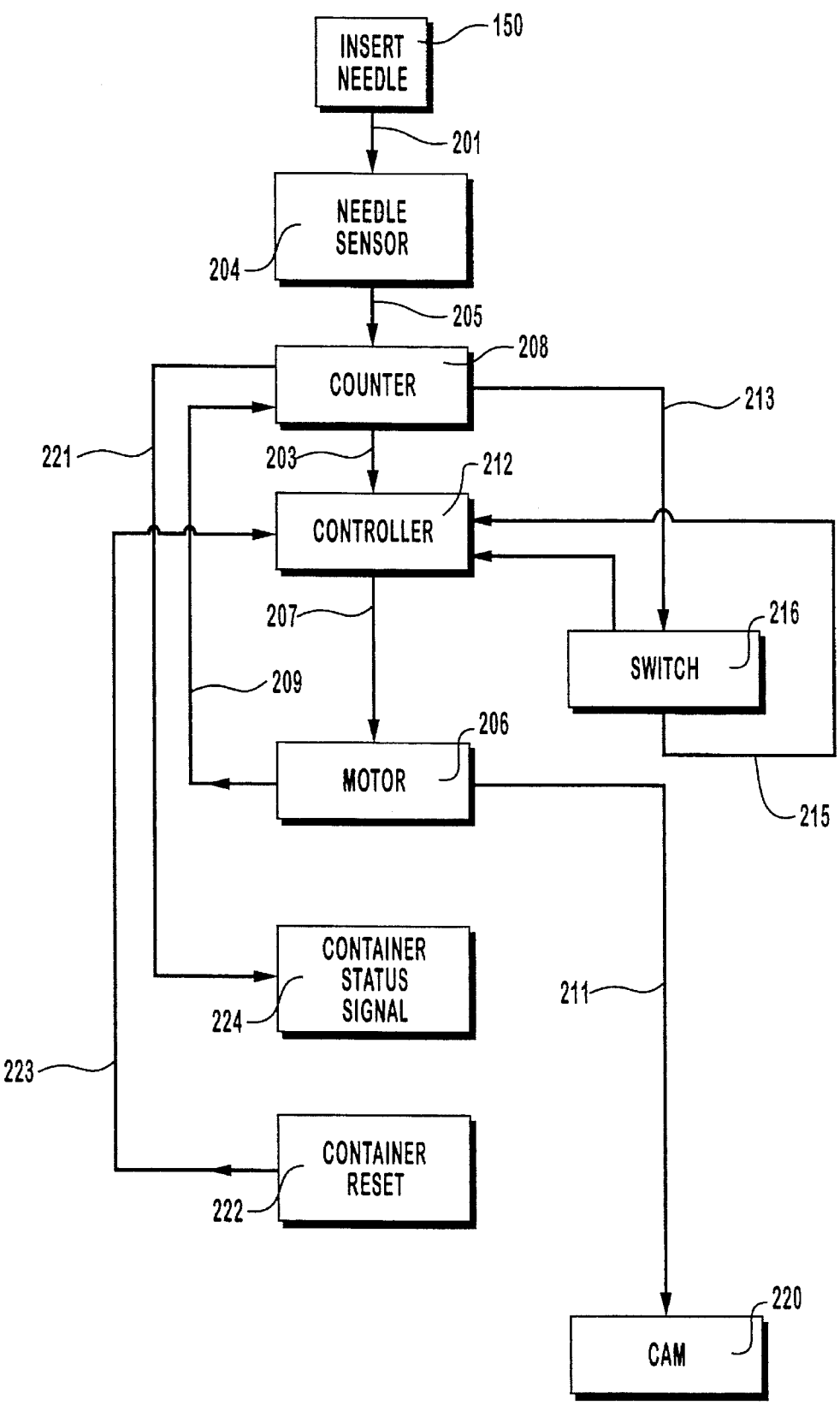
FIG. 2 shows a block diagram of the system for another embodiment of the present invention.

FIG. 2 shows a second embodiment 200 of the present invention showing a single counter 208. Although the counter 208 is shown separately, it can be formed as part of the controller which may be an "eprom" microcontroller. A first feedback loop links the electric motor 206 to the controller through counter 208 by lines 207, 209 and 203. The motor start cycle is triggered by the presence of needle 50 in needle sensor 204 which is linked to the counter 208 by line 205. Actuation of the motor 206 causes the rotation of shaft 220.

A second feedback loop links the counter 208 to switch 216 and to the controller 212 and signal 214 by lines 203, 213, 215 and 209 as shown in FIG. 2. The switch 216 has its signal fed to controller 212 by line 217 so that the controller will not drive the motor until the switch 216 is reset or replaced.

FIGS. 1 and 2 show the counter or counters as separate devices from the microcontrollers. In practice, an integrated circuit or circuits will be used to constitute the microcontroller. Thus the counter or counters and feedback loops may be contained on one or more integrated circuit chips. The actual control of the micro-circuits may be obtained by fixing the operation of one or more so-called "eproms". It is well within the skill of the electrical engineers and art to use commercially available circuit elements to achieve the functions taught by the present invention without requiring any invention by the user.

Figure 3:
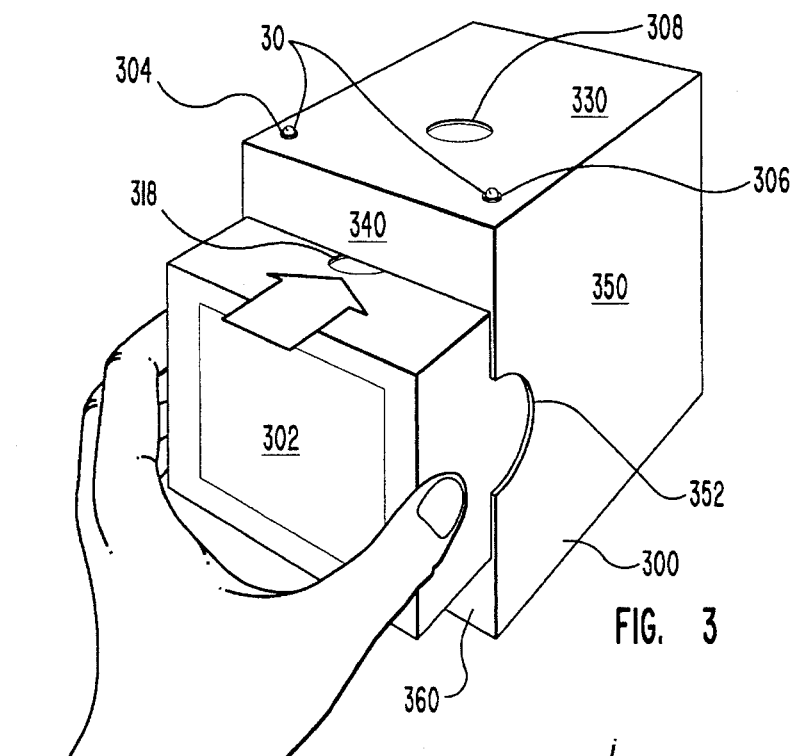
FIGS. 3 and 4 are front perspectives of an embodiment 300 of the present invention showing the removable needle storage box (safe) in FIG. 3 and the insertion of a needle for removal in FIG. 4.
Figure 4:
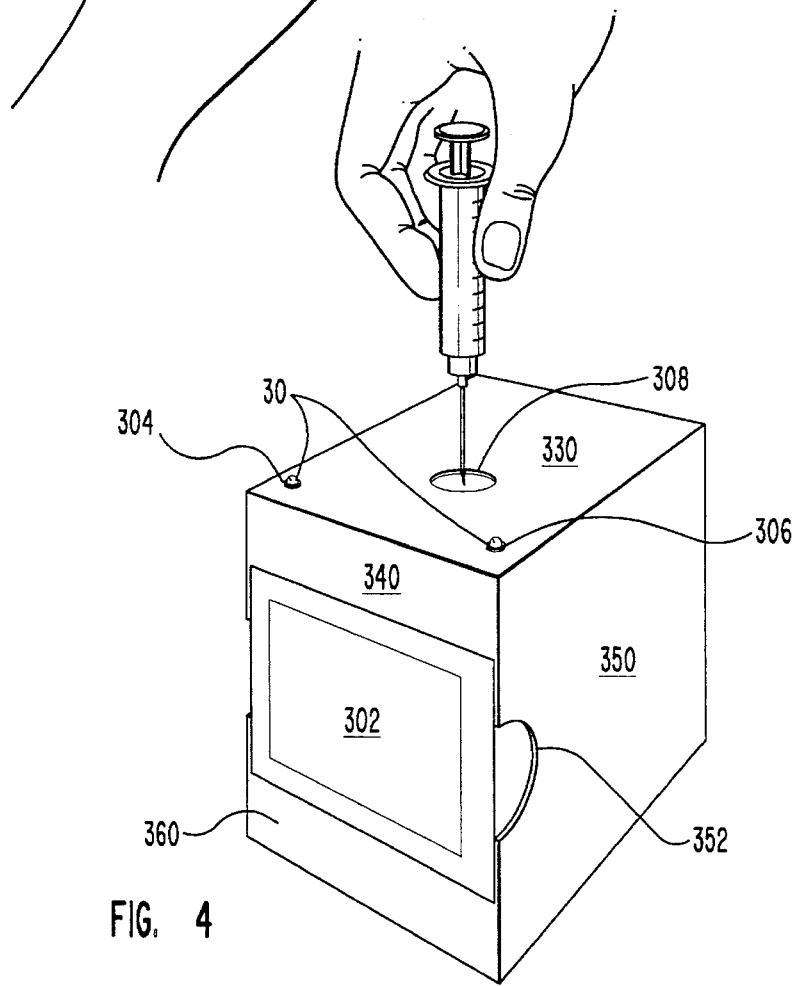

The outer physical structure of one embodiment of the present invention is shown in FIGS. 3 and 4. An outer cover shown generally by 300 has side walls 350, a base section 360 and an upper section 340 with a top 330. The top has signal apertures 310 formed therein for permitting signal lights 304 and 306 to fit through, A needle aperture 308 is also formed in the top section 330.

A needle disposal container (safe) 302 has a closable needle receiver 318 formed therein which aligns with the needle aperture 308 formed in the box 300. Arcs 352 are formed in the sides 350 of the cover for making it easier to grasp the needle disposal box.

FIG. 4 shows the needle disposal container (safe) nested fully in the outer cover of the outer box with a needle 322 attached to a syringe 320 being placed in the aperture 308 to commence actuation of the device (system).

Figure 5:
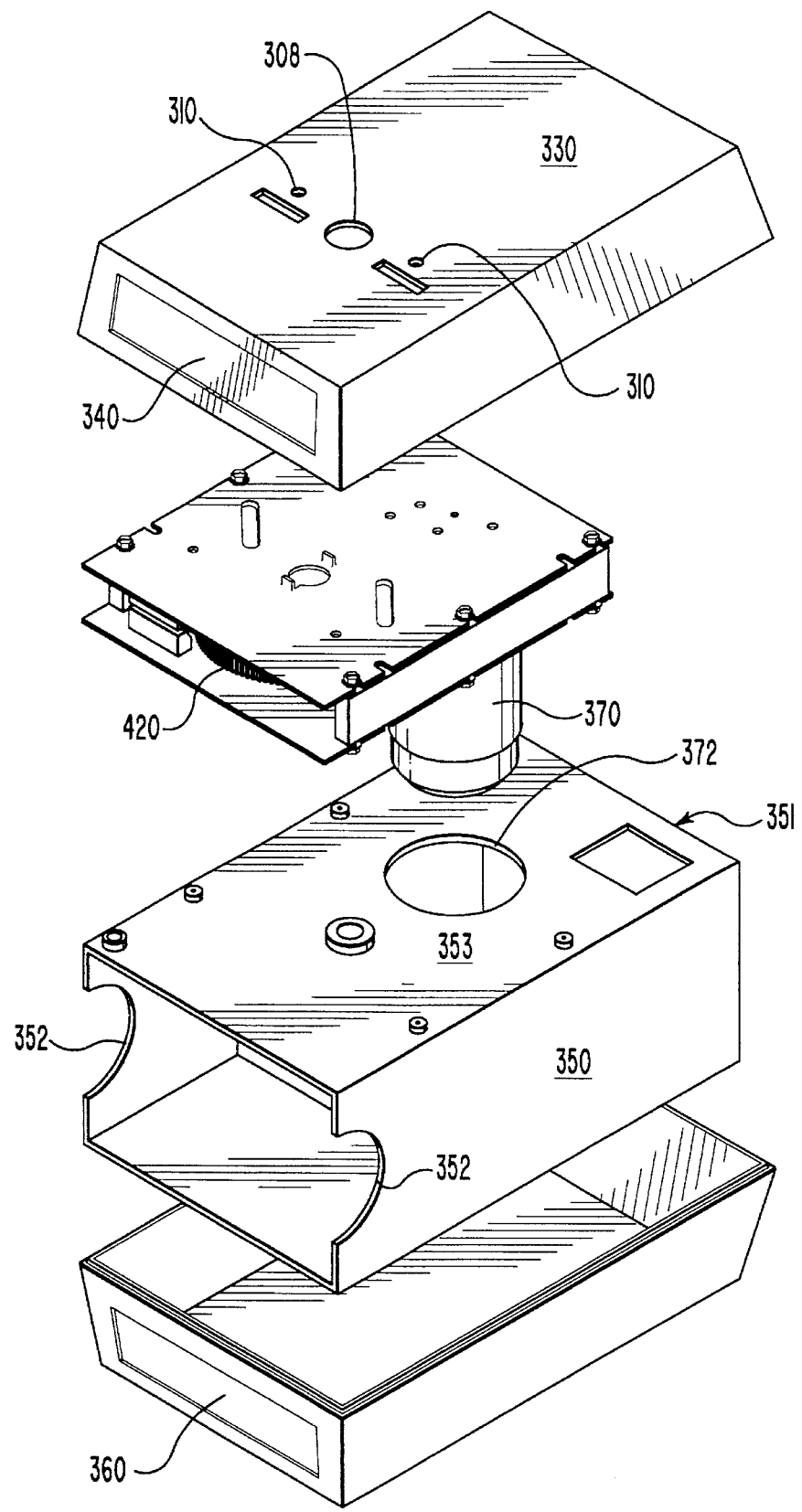
FIG. 5 shows an exploded front perspective view of an embodiment 300 of the present invention with the needle storage box removed (safe).

FIG. 5 shows an exploded view of the outer cover 300 in which an electric motor 370 fits through an opening 372 formed in intermediate section 351. Motor 370 turns gear 420 and is mounted securely and fixedly on upper surface 353 of intermediate section 351.

Figure 6:
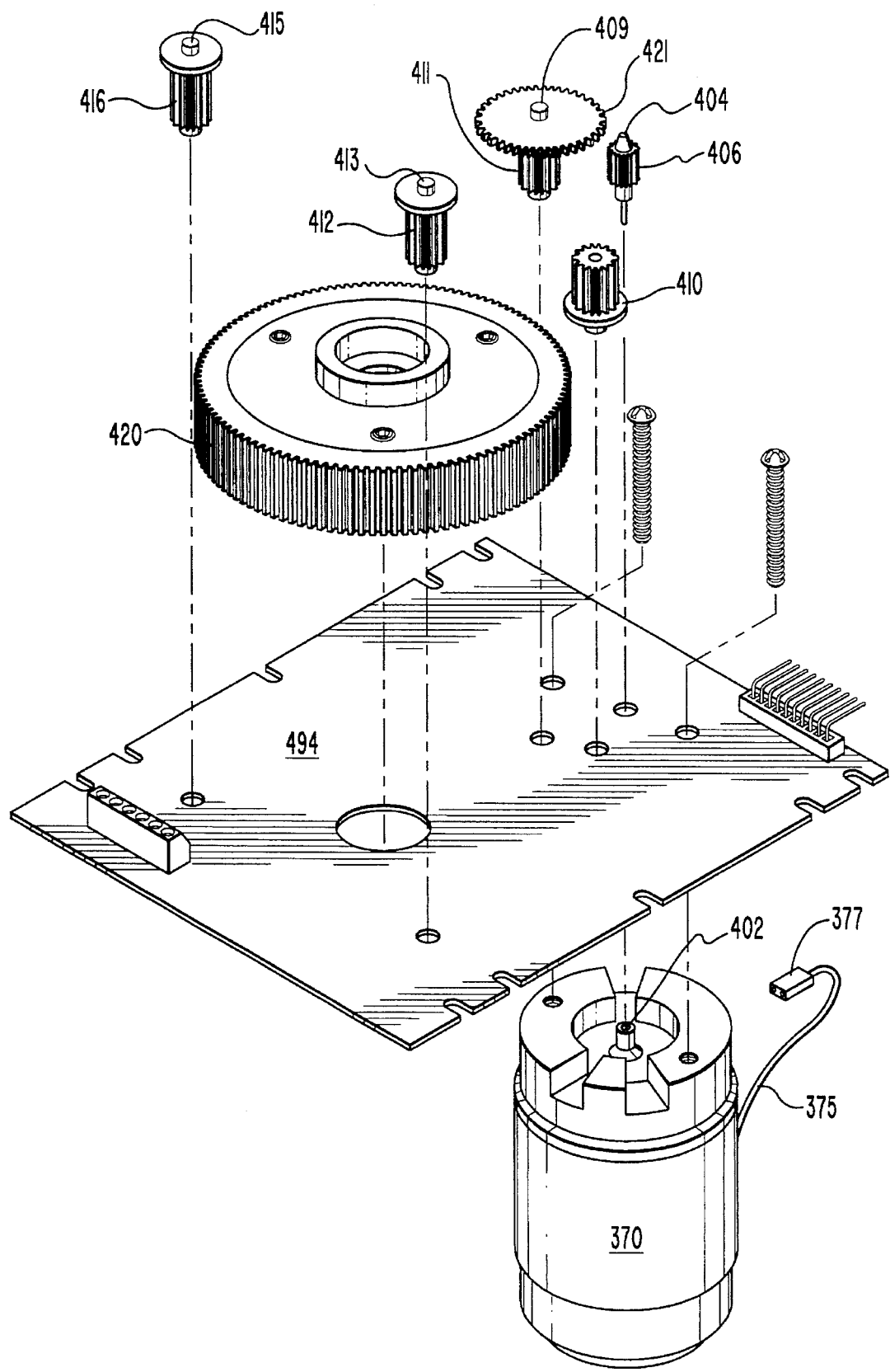
FIGS. 6 and 7 show an exploded front perspective of an embodiment 300 of the present invention showing the detail of the construction of the motor and gear assembly in FIG. 6 and the motor, gear and spacer assembly in FIG. 7.
Figure 7:
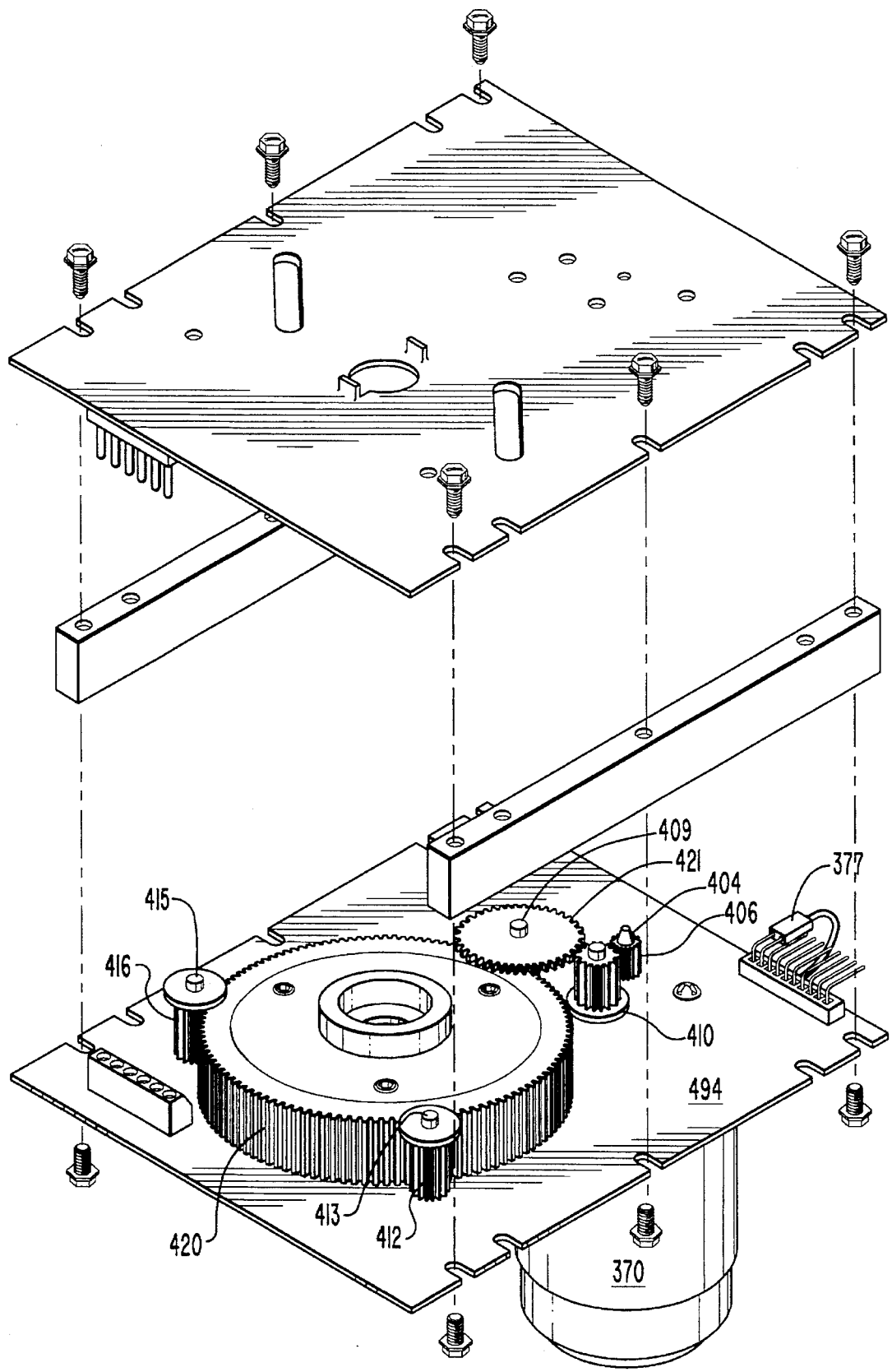
Figure 8:
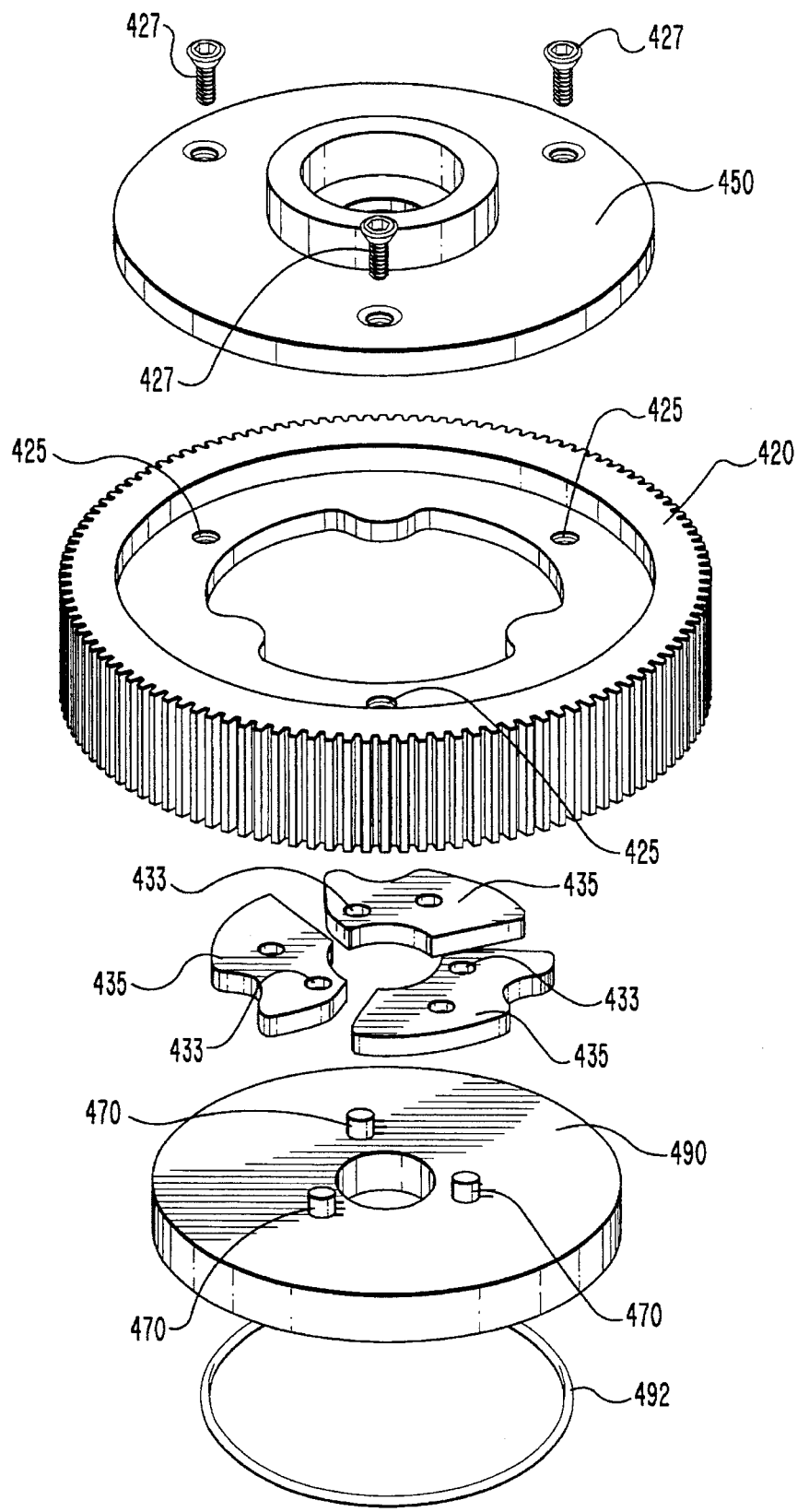
FIG. 8 shows an exploded view of the cam and gear assembly shown in FIGS. 6 and 7.

The structural interrelationship between the motor, the gears and the cams is shown clearly in the exploded views of FIGS. 6, 7 and 8. The output shaft 402 of the motor corresponds to the output shafts 120 and 220 in FIGS. 1 and 2. The motor receives its electrical power and control through wires 375 fixed to connector 377 which mates with the output of the microcontroller 112, 212 shown in FIGS. 1 and 2.

Motor 370 is fastened to plate 494 with shaft 402 driving gear 410 which in turn drives gear 406 mounted on shaft 404. Gear 406 drives gear 421 mounted on shaft 411 which drives gear 420 through gear 411. Gear 420 also engages gears 416 and 412 which are mounted on shafts 415 and 413 respectively. Gear 420 has three channels formed in it for permitting three screws 427 to reach therethrough to engage channels 437 formed in eccentrically mounted lobes or cams 435 which are mounted on shafts 470 for rotation about those shafts. A friction or clutch member 492 is sandwiched between the underside of gear 420 and the upper side of base plate 494 to provide resistance to the rotation of gear 420 so that the cams will rotate closed or open to grasp or release the needle hub as desired.

Figure 9:
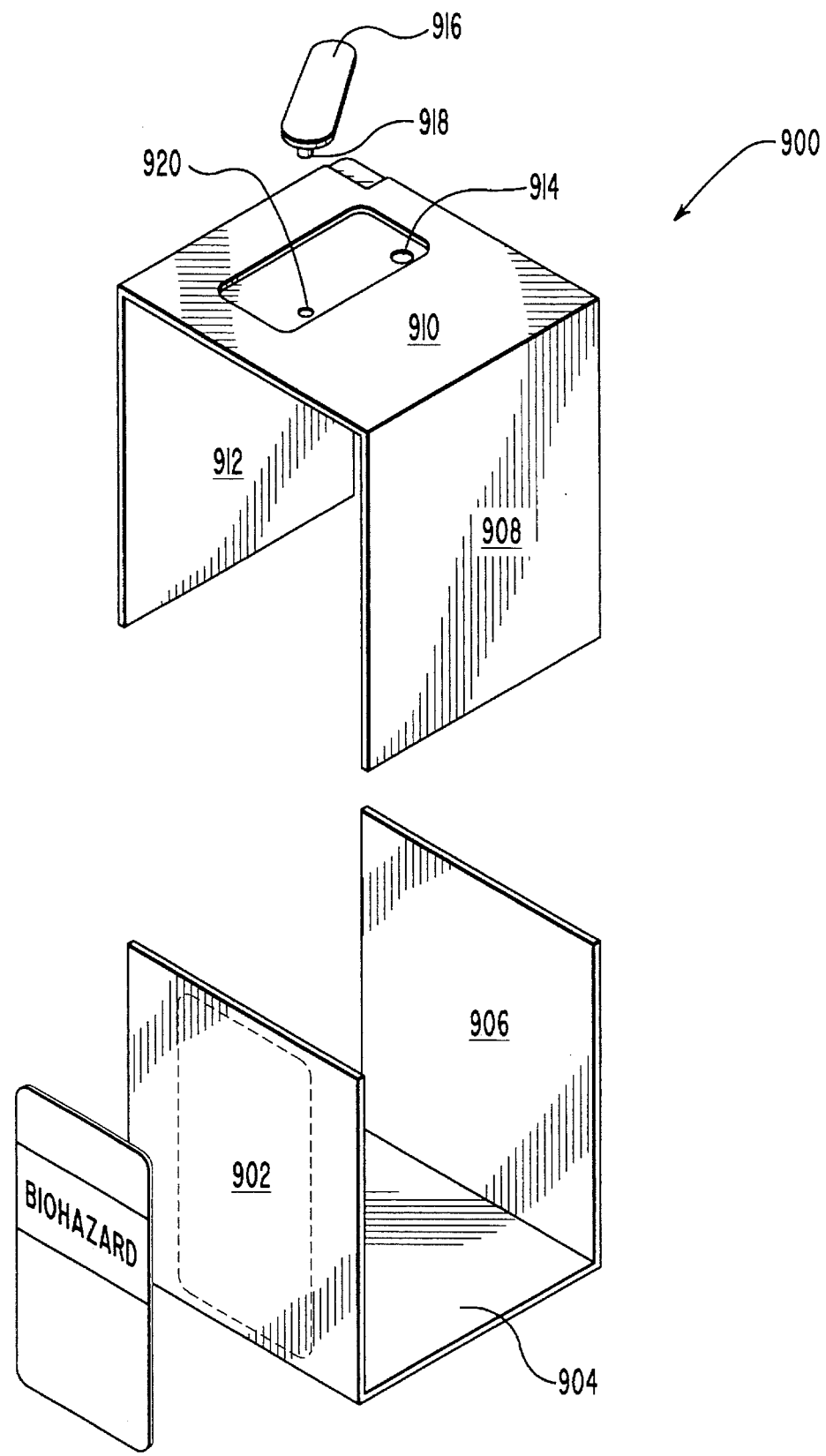
FIG. 9 shows an exploded perspective view of the needle disposal box (safe) shown in FIG. 3.

FIG. 9 shows the safe (in one embodiment) 900 having two "U" shaped members with three sides 902, 904 and 906 and 908, 910, and 914. When the "U" shaped members are joined a closed box is formed. The upper surface 910 has an opening 914 which is aligned with opening 300 of the outer cover and a rotatable locking tab 916 having a locking end 918 which mates with receiver 920 to close and lock opening 914.

The embodiments of the present invention which have been shown and described are illustrative of the main principles of the invention but the following claims shall not be limited to the embodiments shown. The claims are intended to cover and do cover those variations of the invention which are apparent to those skilled in the art.

We claim:

1. An apparatus for removing needles of the type received by medical syringes comprising;

a first housing means;

sensor means contained within the housing means;

needle removing means contained within said first housing means that includes an electric motor with said first housing means and having a rotating output shaft that mounts a plurality of cam members, each mounted for rotation and revolution about an axis which defined a passageway into said first housing means through which a needle can be inserted for gripping and rotation by said cam members;

second housing means for containing removed needles;

feedback control means for interconnecting said sensor means and said needle removing means such that when said sensor means detects a needle, said needle removing means removes said needle and permits it to drop into said second housing means.

2. The needle removing means claimed in claim 1 further including:

counting means contained with the first housing means for counting the number of needles removed by the needle removing means.

3. The needle removing means claimed in claim 1 further including:

switch means for rendering inoperative the needle removing means.

4. The needle removing means claimed in claim 1 further including signalling means connected to the first housing means to be activated by the feedback control means when the second housing means is indicated to be nearly full of removed needles.

5. A needle removing apparatus for removing medical needles comprising:

a first housing means;

a needle storage box means;

an electric motor contained within the housing means having a rotating output shaft that mounts a plurality of cam members, each mounted for rotation and revolution about an axis which defines a passageway into said first housing means through which a needle can be inserted for gripping and rotation by said cam members;

a needle sensor means disposed within said first housing means;

a programmable controller means for receiving an electrical input from said sensor means and having an electrical output for controlling said electric motor; and said programmable controller means having counting and memory means for counting the number of needles inserted into said apparatus and for counting the number of turns of the rotating output shaft means, which said programmable controller means is operative to control the number of rotations of said electric motor means and the number of needles received in said needle storage box means.

6. The needle removing means claimed in claim 5 further including:

portable electric power means contained adjacent the first housing means;

first and second electric signalling means contained by the first housing means for signalling when said portable power source output is below a predetermined level and when the number of needles stored is at a predetermined level.

7. The needle removing means claimed in claim 1 further including;

means for sensing when said second housing means is not fitted to said first housing means.

8. The needle removing means claimed in claim 5 further including;

means for sensing when said second housing means is not fitted to said first housing means.

9. The needle removing means claimed in claim 5 further including;

first storage sensing means for determining when a needle storage box means is installed to said first housing and is ready to receive needles.

\* \* \* \* \*